United States Patent
Bright et al.

(10) Patent No.: US 6,200,979 B1
(45) Date of Patent: *Mar. 13, 2001

(54) METHODS OF ADMINISTERING CRF ANTAGONISTS

(76) Inventors: Gene M. Bright, 329 Tyler Ave., Groton, CT (US) 06340; Yuhpyng L. Chen, 8 Waterview Dr., Waterford, CT (US) 06385; Willard M. Welch, 116 Pequot Ave., Mystic, CT (US) 06355

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/796,096

(22) Filed: Feb. 5, 1997

Related U.S. Application Data

(62) Division of application No. 08/259,835, filed on Jun. 15, 1994, now Pat. No. 5,646,152.

(51) Int. Cl.$^7$ .................................................. A61K 31/505
(52) U.S. Cl. ......................... 514/258; 514/307; 514/341; 514/406; 514/407
(58) Field of Search ................................... 514/406, 407, 514/341, 258, 307

(56) References Cited

U.S. PATENT DOCUMENTS

| 4,605,642 | 8/1986 | Rivier et al. . |
| 5,063,245 | 11/1991 | Abrev et al. . |
| 5,464,847 | 11/1995 | Courtemanche et al. . |

FOREIGN PATENT DOCUMENTS

| 2430454 | 1/1976 | (DE) . |
| 3145287 | 5/1983 | (DE) . |

*Primary Examiner*—Samuel Barts
(74) *Attorney, Agent, or Firm*—Peter C. Richardson; Paul H. Ginsburg; A. David Joran

(57) ABSTRACT

Substituted pyrrazoles of the formula

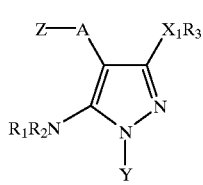

I wherein $R_1$, $R_2$, $R_3$, X, Y, Z and A are as defined herein with reference to formula I; pyrazoles and pyzazolopyrimidines of the formula

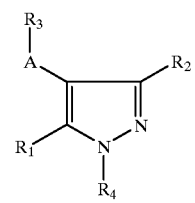

VII wherein $R_1$, $R_2$, $R_3$, $R_4$ and A are defined herein with reference to formula VII; compounds of the formula

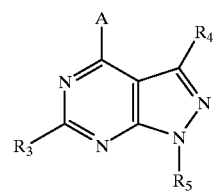

VIII wherein A, $R_3$, $R_4$ and R. are as defined herein with reference to formula VIII; and pyrrolopyzimidines of the formula

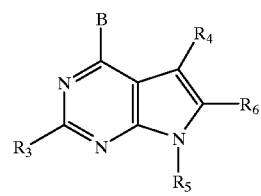

IX wherein B1 R3, R4, R5 and R6 are as defined herein, with reference to formula IX, have corticotropin-releasing factor antagonist activity and as such are of use in the treatment of a variety of stress-related disorders.

7 Claims, No Drawings

METHODS OF ADMINISTERING CRF ANTAGONISTS

This application is a Division od Ser. No. 08/259,835, filed Jun. 15, 1994, now U.S. Pat. No. 5,646,152.

BACKGROUND OF THE INVENTION

The present invention relates to the treatment of certain illnesses by administering novel corticortropin-releasing factor (CRF) antagonists.

CRF antagonists are mentioned in U.S. Pat. Nos. 4,605,642 and 5,063,245 referring to peptides and pyrazolinones, respectively. The importance of CRF antagonists is set out in the literature, e.g. as discussed in U.S. Pat. No. 5,063,245. A recent outline of the different activities possessed by CRF antagonists is found in M. J. Owens et al., Pharm. Rev., Vol. 43, pages 425 to 473 (1991).

The CRF antagonists administered according to the invention are described in copending patent application Ser. Nos. PCT/US 93/10716, PCT/US93/01539, PCT/US93/11333, and PCT/US93/10715, all of which are incorporated herein by reference.

SUMMARY OF THE INVENTION

The present invention relates to the treatment of certain illnesses which comprises administering to a subject in need of such treatment an effective amount of a compound of the formula (A)

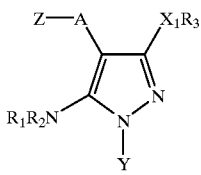

I and the pharmaceutically acceptable acid addition salts thereof,
wherein A is $CH_2$;

R$_1$, R$_2$ and R$_3$ are each independently linear $C_1$–$C_5$ alkyl, branched $C_3$–$C_8$ alkyl, $C_3$–$C_8$ alkenyl wherein the double bond is not adjacent to the N or $X_1$ when $X_1$ is oxygen or sulfur, or $C_3$–$C_7$ cycloalkyl $(CH_2)n$ wherein n is 0, 1, 2, 3 or 4; or R$_1$ and R$_2$ when taken together with the nitrogen form a saturated four, five or six membered ring optionally condensed with benzo; and R$_3$ may also be $(CH_2)_qQ_1R_{19}$ wherein q is 0, 1 or 2, $Q_1$ is O, S, NH, N($C_1$–$C_6$ alkyl) or a covalent bond when $X_1$ is not a covalent bond, and $R_{19}$ is hydrogen, linear $C_1$–$C_6$ alkyl, branched $C_3$–$C_8$ alkyl, $C_3$–$C_8$ alkenyl, $C_3$–$C_8$ cycloalkyl or $C_3$–$C_6$ cycloalkyl $(CH_2)n$ wherein n is 1 to 4;

$X_1$ is a covalent bond, $CH_2$, NR wherein R is hydrogen or linear $C_1$–$C_6$ alkyl, O, or S;

Y is phenyl, thienyl, benzothienyl, pyridyl, quinolyl, pyrazinolyl, pyrimidyl, imidazolyl, benzimidazolyl, furanyl, benzofuranyl, thiazolyl, benzothiazolyl, isothiazolyl, benzisothiazolyl, isoxazolyl, benzisoxazolyl, triazolyl, pyrazolyl, pyrrolyl, indolyl, azaindolyl, oxazolyl, benzoxazolyl, pyrrolidinyl, thiazolidinyl, morpholinyl, or piperidinyl, each of which may be substituted by one to three of any one of fluoro, chloro, bromo, or methyl, or one of trifluoromethyl; with the proviso that Y is not unsubstituted phenyl; and Z is
(a)

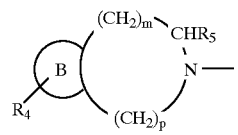

II wherein the B ring is phenyl, naphthyl, pyridyl, pyrimidinyl, pyrazinyl, pyridazinyl, triazilyl, pyrrolyl, pyrazolyl, imidazolyl, triazolyl, thienyl, or indolyl, each of which may be substituted by methyl, methoxy, fluoro, chloro, bromo or iodo; or a saturated 5- or 6-membered carbocyclic ring or a partially unsaturated ring having one or two double bonds;

R$_4$ is hydrogen, $C_1$–$C_6$ alkyl, $C_1$–$C_6$ alkoxy, or hydroxy, fluoro, chloro, bromo, iodo, or trifluoromethyl;

R$_5$ is hydrogen, linear $C_1$–$C_6$ alkyl, branched $C_3$–$C_8$ alkyl, $C_3$–$C_8$ alkenyl, or $(CH_2)_o$—$X_2$—$(CH_2)_r$—$Q_2$—$R_6$;

R$_6$ is hydrogen, linear $C_1$–$C_6$ alkyl, branched $C_3$–$C_8$ alkyl, or $C_3$–$C_8$ alkenyl;

$X_2$ and $Q_2$ are each independently O, S, NH, N($C_1$–$C_6$ alkyl), or one of $X_2$ and Q may be a covalent bond;

m is 0 or 1;
o is 1 or 2;
p is 1 or 2;
r is 0, 1, or 2;

(b)

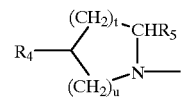

III wherein R$_4$ and R5 are as defined above, and t and u are each independently 1 or 2;

(c) —NR$_7$R$_8$ wherein R$_7$ and RB are each independently hydrogen, $C_1$–$C_6$ linear alkyl, branched $C_3$–$C_8$ alkyl, $C_3$–C, alkenyl, $(CH_2)_vCH_2OH$, $(CH_2)_vNR_9R_{10}$, wherein v is 0 to 3, and R$_9$ and R$_{10}$ are each independently hydrogen, or linear $C_1$–$C_6$ alkyl; $C_1$–$C_{12}$ cycloalkyl, ($C_3$–$C_{12}$ cycloalkyl) $(CH_2)_n$, ($C_6$–$C_{10}$ bicycloalkyl) $(CH_2)_n$, wherein n is 0 to 4, benzofused $C_3$–$C_6$ cycloalkyl, $C_1$–$C_6$ hydroxyalkyl, phenyl, phenyl ($C_1$–$C_3$ alkylene), each of which may be substituted by one or two of hydroxy, fluoro, chloro, bromo, $C_1$–$C_5$ alkyl, or $C_1$–$C_5$ alkoxy; or R$_7$ and R$_8$ may be taken together with the nitrogen to form a saturated or partially unsaturated 5- to 7-membered ring which may contain one of O, S, NH or N($C_1$–$C_6$ alkyl) and which may be substituted by $C_1$–$C_6$ alkyl, hydroxy or phenyl wherein any double bond(s) are not adjacent to any heteroatoms;

(d)

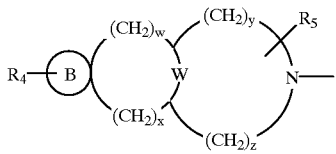

IV wherein B, $R_4$ and $R_5$ are as defined above, w, x, y and z are each independently 1 or 2, and W is $(CH_2)_q$ wherein q is as defined above, $N(C_1-C_6$ alkyl), or oxygen;

(e)

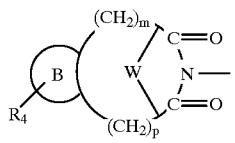

V wherein B, $R_4$, m and p are as defined above;

(f)

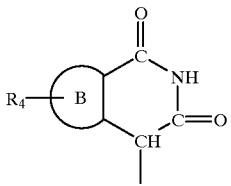

VI wherein B and $R_4$ are as defined above;

(g) $O(CH_2)_vR_{11}$
wherein v is 0 to 3 and $R_{11}$ is linear $C_1-C_6$ alkyl, branched $C_3-C_8$ alkyl, phenyl, naphthyl, 1,2,3,4-tetrahydronaphthyl, thienyl, benzothienyl, pyridyl, quinolyl, pyrazinolyl, pyrimidyl, imidazolyl, benzimidazolyl, furanyl, benzofuranyl, thiazolyl, benzothiazolyl, isothiazolyl, benzisothiazolyl, isoxazolyl, benzisoxazolyl, triazolyl, pyrazolyl, pyrrolyl, indolyl, azaindolyl, oxazolyl, benzoxazolyl, pyrrolidinyl, thiazolidinyl, morpholinyl, piperidinyl, or thienyl, each of which may be substituted by one or two of any one of fluoro, chloro, bromo, methyl, or trifluoromethyl;

(B)

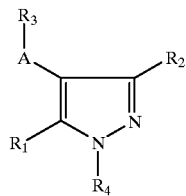

VII and the pharmaceutically acceptable acid addition salts thereof, wherein
   A is C=O or $SO_2$, or A and $R_1$ together with the carbons to which they are attached form pyrimidinyl or 5-pyridyl which may be substituted by $R_5$ which is hydrogen, $C_1-C_6$ alkyl, fluoro, chloro, bromo, hydroxy, amino, $O(C_1-C_6$ alkyl), $NH(C_1-C_6$ alkyl), $N(C_1-C_6$ alkyl)$(C_1-C_6$ alkyl), SH, $S(O)_n(C_1-C_6$ alkyl) wherein n=0, 1 or 2, wherein said $C_1-C_6$ alkyl may be substituted by from 1 to 3 substituents $R_6$ which is hydroxy, amino, $C_1-C_3$ alkoxy, dimethylamino, diethylamino, methylamino, ethylamino, NH(C=O)$CH_3$, fluoro, chloro, bromo or $C_1-C_3$ thioalkyl;

$R_1$ is hydrogen, $C_1-C_6$ alkyl, amino, $O(C_1-C_6$ alkyl), $NH(C_1-C_6$ alkyl), $N(C_1-C_6$ alkyl)$(C_1-C_6$ alkyl), wherein said $C_1-C_6$ alkyl may be substituted by from 1 to 3 substituents $R_6$ as defined above;

$R_2$ is hydrogen, $C_1-C_6$ alkyl, hydroxy, amino, $O(C_1-C_6$ alkyl), $NH(C_1-C_6$ alkyl), $N(C_1-C_6$ alkyl)$(C_1-C_6$ alkyl), SH, $S(O)_n(C_1-C_6$ alkyl) wherein n=0, 1, or 2, cyano, hydroxy, carboxy, or amido, wherein said alkyls may be substituted by one to three of hydroxy, amino, carboxy, amido, NH(C=O) $(C_1-C_6$ alkyl), $N(C_1-C_6$ alkyl)$(C_1-C_6$ alkyl), (C=O)O $(C_1-C_6$ alkyl), $C_1-C_3$ alkoxy, $C_1-C_3$ thioalkyl, fluoro, bromo, chloro, iodo, cyano or nitro;

$R_3$ is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, pyridinyl, tetrazolyl, or 9 to 12 membered bicycloalkyl, optionally containing one to three of O, S or N—Z wherein Z is hydrogen, $C_1-C_4$ alkyl, $C_1-C_4$ alkanoyl, phenyl or phenylmethyl, wherein each one of the above groups may be substituted independently by from one to three of fluoro, chloro, bromo, $C_1-C_6$ alkyl, $C_1-C_6$ alkoxy, or trifluoromethyl, or one of cyano, nitro, amino, $NH(C_1-C_6$ alkyl), $N(C_1-C_4$ alkyl)$(C_1-C_2$ alkyl), COO $(C_1-C_4$ alkyl), CO$(C_1-C_4$ alkyl), $SO_2NH(C_1-C_4$ alkyl), $SO_2N(C_1-C_4$ alkyl)$(C_1-C_2$ alkyl), $SO_2NH_2$, $NHSO_2(C_1-C_4$ alkyl), $S(C_1-C_6$ alkyl), $SO_2(C_1-C_6$ alkyl), wherein said $C_1-C_4$ alkyl and $C_1-C_6$ alkyl may be substituted by one or two of fluoro, chloro, hydroxy, amino, methylamino, dimethylamino or acetyl; and $R_4$ is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, pyridinyl, tetrazolyl, or 3 to 8-membered cycloalkyl or 9 to 12-membered bicycloalkyl, optionally containing one to three of O, S or N—Z wherein Z is hydrogen, $C_1-C_4$ alkyl, $C_1-C_4$ alkanoyl, phenyl or phenylmethyl, wherein each of the above groups may be substituted independently by from one to three of fluoro, chloro, bromo, trifluoromethyl, $C_1-C_6$ alkyl or $C_1-C_6$ alkoxy, or one of cyano, nitro, amino, $NH(C_1-C_6$ alkyl), $N(C_1-C_4$ alkyl)$(C_1-C_2$ alkyl), COO$(C_1-C_4$ alkyl), CO$(C_1-C_4$ alkyl), $SO_2NH(C_1-C_4$ alkyl), $SO_2N(C_1-C_4$ alkyl)$(C_1-C_2$ alkyl), $SO_2NH_2$, $NH_2SO_2(C_1-C_4$ alkyl), $S(C_1-C_6$ alkyl), $SO_2(C_1-C_6$ alkyl), wherein said $C_1-C_4$ alkyl and $C_1-C_6$ alkyl may be substituted by one or two of fluoro, chloro, hydroxy, amino, methylamino, dimethylamino or acetyl; provided that (1) $R_4$ is not unsubstituted phenyl; (2) when $R_1$ is amino, $R_2$ is methylthio, $R_4$ is 2,4,6-trichlorophenyl, and A is C=0, then $R_3$ is not 2-chlorophenyl; and (3) $R_1$ and $R_2$ are not both hydrogen;

(C)

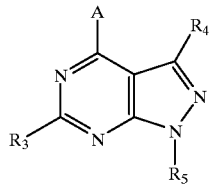
VIII and the pharmaceutically acceptable acid addition salts thereof, wherein A is $NR_1R_2$, $CR_1R_2R_{11}$, or $C(=CR_1R_{12})R_2$, $NHCR_1R_2R_{11}$, $OCR_1R_2R_{11}$, $SCR_1R_2R_{11}$, $NHNR_1R_2$, $CR_2R_{11}NHR_1$, $CR_2R_{11}OR_1$, $CR_2R_{11}SR_1$ or $C(O)R_2$;

$R_1$ is hydrogen, or $C_1$–$C_6$ alkyl which may be substituted by one or two substituents $R_6$ independently selected from the group consisting of hydroxy, fluoro, chloro, bromo, iodo,

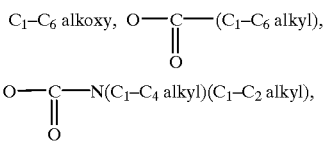

amino, $NH(C_1$–$C_4$ alkyl), $N(C_1$–$C_2$ alkyl)($C_1$–$C_4$ alkyl), $S(C_1$–$C_6$ alkyl), $OC(O)NH(C_1$–$C_4$ alkyl), $N(C_1$–$C_2$ alkyl)$C(O)(C_1$–$C_4$ alkyl), $NHC(C_1$–$C_4$ alkyl) with =O,

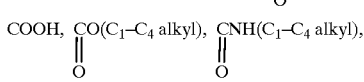

$CN(C_1$–$C_4$ alkyl)($C_1$–$C_2$ alkyl) with =O, SH, CN, $NO_2$, $SO(C_1$–$C_4$ alkyl), $SO_2(C_1$–$C_4$ alkyl), $SO_2NH(C_1$–$C_4$ alkyl), $SO_2N(C_1$–$C_4$ alkyl)($C_1$–$C_2$ alkyl), and said $C_1$–$C_6$ alkyl may contain one or two double or triple bonds;

$R^2$ is $C_1$–$C_{12}$ alkyl, aryl or ($C_1$–$C_{10}$ alkylene)aryl wherein said aryl is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, azaindolyl, oxazolyl, or benzoxazolyl; 3- to 8-membered cycloalkyl or ($C_1$–$C_6$ alkylene) cycloalkyl, wherein said cycloalkyl may contain one or two of O, S or N—Z wherein Z is hydrogen, $C_1$–$C_4$-alkyl, benzyl or $C_1$–$C_4$ alkanoyl, wherein $R^2$ may be substituted independently by from one to three of chloro, fluoro, or $C_1$–$C_4$ alkyl, or one of hydroxy, bromo, iodo, $C_1$–$C_6$ alkoxy, $NH(C_1$–$C_2$ alkyl), $N(C_1$–$C_2$ alkyl)($C_1$–$C_4$ alkyl), $N(C_1$–$C_4$ alkyl)$C(C_1$–$C_4$ alkyl) with =O, $NHC(C_1$–$C_4$ alkyl) with =O, COOH, $CO(C_1$–$C_4$ alkyl), $CNH(C_1$–$C_4$ alkyl), (with =O)

$CN(C_1$–$C_4$ alkyl)($C_1$–$C_2$ alkyl) with =O, SH, CN, $NO_2$, $SO(C_1$–$C_4$ alkyl), $SO_2(C_1$–$C_4$ alkyl), $SO_2NH(C_1$–$C_4$ alkyl), $SO_2N(C_1$–$C_4$ alkyl)($C_1$–$C_2$ alkyl), and wherein said $C_1$–$C_{12}$ alkyl or $C_1$–$C_{10}$ alkylene may contain one to three double or triple bonds; or $NR_1R_2$ or $CR_1R_2R_{11}$ may form a 4- to 8-membered ring optionally containing one or two double bonds or one or two of O, S or N—Z wherein Z is hydrogen, $C_1$–$C_4$ alkyl, benzyl, or $C_1$–$C_4$ alkanoyl;

$R_3$ is hydrogen, $C_1$–$C_6$ alkyl, fluoro, chloro, bromo, iodo, hydroxy, amino, $O(C_1$–$C_6$ alkyl), $NH(C_1$–$C_6$ alkyl), $N(C_1$–$C_4$ alkyl)($C_1$–$C_2$ alkyl), SH, $S(C_1$–$C_4$ alkyl), $SO(C_1$–$C_4$ alkyl), or $SO_2(C_1$–$C_4$ alkyl), wherein said $C_1$–$C_4$ alkyl and $C_1$–$C_6$ alkyl may contain one or two double or triple bonds and may be substituted by from 1 to 3 substituents $R_7$ independently selected from the group consisting of hydroxy, amino, $C_1$–$C_3$ alkoxy, dimethylamino, diethylamino, methylamino, ethylamino,

fluoro, chloro or $C_1$–$C_3$ thioalkyl;

$R_4$ is hydrogen, $C_1$–$C_6$ alkyl, fluoro, chloro, bromo, iodo, $C_1$–$C_6$ alkoxy, amino, $NH(C_1$–$C_6$ alkyl), $N(C_1$–$C_6$ alkyl)($C_1$–$C_2$ alkyl), $SO_n(C_1$–$C_6$ alkyl), wherein n is 0, 1 or 2, cyano, hydroxy, carboxy, or amido, wherein said $C_1$–$C_6$ alkyls may be substituted by one to three of hydroxy, amino, carboxy, amido, $NHC(C_1$–$C_4$ alkyl) with =O, $NH(C_1$–$C_4$ alkyl), $N(C_1$–$C_4$ alkyl)($C_1$–$C_2$ alkyl), $CO(C_1$–$C_4$ alkyl) with =O, $C_1$–$C_3$ alkoxy, $C_1$–$C_3$ thioalkyl, fluoro, bromo, chloro, iodo, cyano or nitro;

$R_5$ is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, pyrrolopyridyl benzoxazolyl, oxazolyl, pyrrolidinyl, thiazolidinyl, piperazinyl, piperidinyl, tetrazolyl, or 3- to 8-membered cycloalkyl or 9- to 12-membered bicycloalkyl, optionally containing one or two of O, S or N—Z wherein Z is hydrogen, $C_1$–$C_4$ alkyl, $C_1$–$C_4$ alkanoyl, phenyl or benzyl, wherein each one of the above groups may be substituted independently by from one to three of fluoro, chloro, bromo, formyl, $C_1$–$C_6$ alkyl, $C_1$–$C_6$ alkoxy or trifluoromethyl, or one of hydroxy, iodo, cyano, nitro, amino, cyclopropyl, $NH(C_1$–$C_4$ alkyl), $N(C_1$–$C_4$ alkyl) ($C_1$–$C_2$ alkyl), $COO(C_1$–$C_4$ alkyl), $CO(C_1$–$C_4$ alkyl), SO$_2$NH(C$_1$–C$_4$ alkyl), SO$_2$N(C$_1$–C$_4$ alkyl)(C$_1$–C$_2$ alkyl), SO$_2$NH$_2$, NHSO$_2$(C$_1$–C$_4$ alkyl), S(C$_1$–C$_6$ alkyl), SO$_2$(C$_1$–C$_6$ alkyl), wherein said C$_1$–C$_4$ alkyl and C$_1$–C$_6$ alkyl may have one double or triple bond and may be substituted by one or two of fluoro, chloro, hydroxy, amino, methylamino, dimethylamino or acetyl; with the proviso that R$_5$ is not unsubstituted phenyl;

R$_{11}$ is hydrogen, hydroxy, fluoro, chloro, COO(C$_1$–C$_2$ alkyl), cyano, or CO(C$_1$–C$_2$ aklyl); and R$_{12}$ is hydrogen or C$_1$–C$_4$ alkyl;

(a) A is not straight chain C$_1$–C$_{12}$ alkyl;

(b) R$_5$ is not a sugar group;

(c) when R$_3$ and R$_4$ are hydrogen and R$_5$ is chlorophenyl, then A is not NH—CH(CH$_3$)—(CH$_2$)$_3$—N(C$_2$H$_5$)$_2$;

(d) when R$_3$ and R$_4$ are hydrogen and A is NR$_1$R$_2$ wherein R$_1$ is C$_3$–C$_7$ cycloalkyl, and R$_2$ is C$_2$–C$_6$ alkenyl, phenyl-(C$_1$–C$_6$ alkylene) or hetero-(C$_1$–C$_6$ alkylene) wherein the hetero radical is furyl, thienyl or pyridinyl, and wherein said phenyl may be substituted by fluoro, chloro, bromo or iodo, then R$_5$ is not tetrahydrofuranyl or tetrahydropyranyl;

(e) when R$_3$ is methoxy, methylthio, or methylsulfonyl, R$_4$ is hydrogen, and R$_5$ is tetrahydrofuranyl or tetrahydropyranyl, then A is not NH(C$_1$–C$_2$alkyl), morpholinyl, hydrazino, or NHC$_2$H$_4$C$_6$H$_5$ which may be substituted by one methyl or two methoxy;

(f) when R$_3$ is hydrogen, C$_1$–C$_6$ alkyl, hydrazino, chloro, bromo, SH, or S (C$_1$–C$_4$ alkyl), R$_4$is hydrogen and R. is C$_3$–C$_8$ cycloalkyl, then A is not hydrazino, NH(C$_1$–C$_2$ alkyl) or N(C$_1$–C$_6$ alkyl) (C$_1$–C$_{12}$ alkyl);

(g) when R$_3$ and R$_4$ are hydrogen and A is NH(CH$_2$)$_m$ COOH wherein m is 1–12, then R$_5$ is not phenyl substituted by one of fluoro, chloro, bromo or iodo;

(h) when R$_3$ is hydrogen, hydroxy, methylthio, chloro or NHbenzyl, R$_4$ is hydrogen, and R$_5$ is chlorophenyl or bromophenyl, then A is not NH(C$_1$–C$_{12}$ alkyl), NHallyl, or N(C$_1$–C$_6$ alkyl) (C$_1$–C$_{12}$ alkyl), wherein said C$_1$–C$_{12}$ alkyl may be substituted by NC$_2$H$_5$, or NH benzyl which may be substituted by one or two bromo, chloro, fluoro, NC$_2$H$_5$ phenyl or morpholinopropyl;

(i) when R$_3$ and R$_4$ are hydrogen and R$_5$ is nitrophenyl, then A is not NHR$_2$ wherein R$_2$ is C$_1$–C$_{12}$ alkyl which may be substituted by two hydroxy, or R$_2$ is phenyl or benzyl;

(j) when R$_3$ is chloro or O(C$_1$–C$_6$ alkyl), R$_4$ is hydrogen, and A is NR$_1$R$_2$ wherein R$_1$ and R$_2$ are independently hydrogen or C$_1$–C$_6$ alkyl, then R$_5$ is not chlorophenyl; and (k) when R$_3$ is hydrogen, A is benzyl or phenethyl, and R$_4$ is fluoro, chloro, bromo or iodo, then R$_5$ is not 5'-deoxy-ribofuranosyl or 5'-amino-5'-deoxy-ribofuranosyl; or (D)

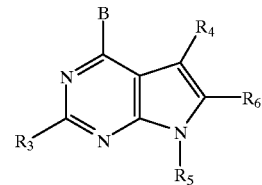

I and the pharmaceutically acceptable acid addition salts thereof, wherein

B is NR$_1$R$_2$, CR$_1$R$_2$R$_{11}$, C(=CR$_2$R$_{12}$)R$_1$, NHCR$_1$R$_2$R$_{11}$, OCR$_1$R$_2$R$_{11}$, SCR$_1$R$_2$R,, NHNR, R$_2$, CR$_2$R$_{11}$ NHR$_1$, CR$_2$R$_{11}$ OR$_1$, CR$_2$R$_{11}$ SR$_1$, or C(O)R$_2$;

R$_1$ is hydrogen, or C$_1$–C$_6$ alkyl which may be substituted by one or two substituents R$_7$ independently selected from the group consisting of hydroxy, fluoro, chloro, bromo, iodo, C$_1$–C$_8$ alkoxy, O—C(=O)—(C$_1$–C$_6$ alkyl), O—C(=O)NH(C$_1$–C$_4$ alkyl), O—C(=O)—N(C$_1$–C$_4$ alkyl)(C$_1$–C$_2$ alkyl), amino, NH(C$_1$–C$_4$ alkyl), N(C$_1$–C$_2$ alkyl)(C$_1$–C$_4$ alkyl), S(C$_1$–C$_6$ alkyl), N(C$_1$–C$_4$ alkyl)C(=O)(C$_1$–C$_4$ alkyl), NHC(=O)(C$_1$–C$_4$ alkyl), COOH, C(=O)O(C$_1$–C$_4$ alkyl), C(=O)NH(C$_1$–C$_4$ alkyl), C(=O)N(C$_1$–C$_4$ alkyl)(C$_1$–C$_2$ alkyl), SH, CN, NO$_2$, SO(C$_1$–C$_4$ alkyl), SO$_2$(C$_1$–C$_4$ alkyl), SO$_2$NH(C$_1$–C$_4$ alkyl), SO$_2$N(C$_1$–C$_4$ alkyl)(C$_1$–C$_2$ alkyl), and said C$_1$–C$_6$ alkyl may contain one or two double or triple bonds;

R$_2$ is C$_1$–C$_{12}$ alkyl, aryl or (C$_1$–C$_{10}$ alkylene)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, pyrrolopyridyl, oxazolyl, or benzoxazolyl; 3- to 8-membered cycloalkyl or (C$_1$–C$_6$ alkylene) cycloalkyl, wherein said cycloalkyl may contain one or two of O, S or N—Z wherein Z is hydrogen, C$_1$–C$_4$ alkyl, benzyl or C$_1$–C$_4$ alkanoyl, wherein R$_2$ may be substituted independently by from one to three of chloro, fluoro, or C$_1$–C$_4$ alkyl, or one of hydroxy, bromo, iodo, C$_1$–C$_6$ alkoxy, O—C(=O)—(C$_1$–C$_6$ alkyl), O—C(=O)—N(C$_1$–C$_4$ alkyl)(C$_1$–C$_2$ alkyl), S(C$_1$–C$_6$ alkyl), NH$_2$, NH(C$_1$–C$_2$ alkyl), N(C$_1$–C$_2$ alkyl)(C$_1$–C$_4$ alkyl), -continued

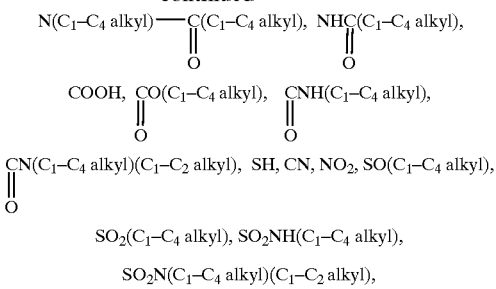

and wherein said $C_1$–$C_{12}$ alkyl or $C_1$–$C_{10}$ alkylene may contain one to three double or triple bonds; or
NR$_1$R$_2$ or CR$_1$R$_2$R$_{11}$, may form a saturated 3- to 8-membered ring of which the 5- to 8-membered ring may contain one or two double bonds or one or two of O, S or N—Z wherein Z is hydrogen, $C_1$–$C_4$ alkyl, benzyl or $C_1$–$C_4$ alkanoyl;
R$_3$ is hydrogen, $C_1$–$C_6$ alkyl, fluoro, chloro, bromo, iodo, hydroxy, amino, O($C_1$–$C_6$ alkyl), NH($C_1$–$C_6$ alkyl), N($C_1$–$C_4$ alkyl)($C_1$–$C_2$ alkyl), SH, S($C_1$–$C_4$ alkyl), SO($C_1$–$C_4$ alkyl), or SO$_2$($C_1$–$C_4$ alkyl), wherein said $C_1$–$C_4$ alkyl and $C_1$–$C_6$ alkyl may contain one double or triple bond and may be substituted by from 1 to 3 substituents R$_8$ independently selected from the group consisting of hydroxy, $C_1$–$C_3$ alkoxy, fluoro, chloro or $C_1$–$C_3$ thioalkyl;
R$_4$ is hydrogen, $C_1$–$C_5$ alkyl, fluoro, chloro, bromo, iodo, $C_1$–$C_6$ alkoxy, amino, NH($C_1$–$C_6$ alkyl), N($C_1$–$C_6$ alkyl)($C_1$–$C_2$ alkyl), SO$_n$($C_1$–$C_6$ alkyl), wherein n is 0, 1 or 2, cyano, hydroxy, carboxy, or amido, wherein said $C_1$–$C_6$ alkyls may be substituted by one hydroxy, trifluoromethyl, amino, carboxy, amido,

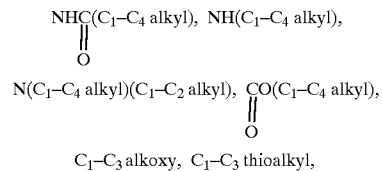

fluoro, bromo, chloro, iodo, cyano or nitro;
R$_5$ is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, pyrrolopyridyl, benzoxazolyl, oxazolyl, pyrrolidinyl, thiazolidinyl, morpholinyl, piperidinyl, piperazinyl, tetrazolyl, or 3- to 8-membered cycloalkyl or 9- to 12-membered bicycloalkyl, optionally containing one or two of O, S or N—Z wherein Z is hydrogen, $C_1$–$C_4$ alkyl, $C_1$–$C_4$ alkanoyl, phenyl or phenylmethyl, wherein each one of the above groups may be substituted independently by from one to three of fluoro, chloro, bromo, formyl, $C_1$–$C_6$ alkyl, $C_1$–$C_6$ alkoxy or trifluoromethyl, or one of hydroxy, iodo, cyano, nitro, amino, NH($C_1$–$C_4$ alkyl), N($C_1$–$C_4$)($C_1$–$C_2$ alkyl), COO($C_1$–$C_4$ alkyl), CO($C_1$–$C_4$ alkyl), SO$_2$NH($C_1$–$C_4$ alkyl), SO$_2$N($C_1$–$C_4$ alkyl)($C_1$–$C_2$ alkyl), SO$_2$NH$_2$, NHSO$_2$($C_1$–$C_4$ alkyl), S($C_1$–$C_6$ alkyl), SO$_2$($C_1$–$C_6$ alkyl), wherein said $C_1$–$C_4$ alkyl and $C_1$–$C_6$ alkyl may be substituted by one or two of fluoro, chloro, hydroxy, $C_1$–$C_4$ alkoxy, amino, methylamino, dimethylamino or acetyl wherein said $C_1$–$C_4$ alkyl and $C_1$–$C_6$ alkyl may contain one double or triple bond; with the proviso that R$_5$ is not unsubstituted phenyl;
R$_6$ is hydrogen, $C_1$–$C_6$ alkyl, fluoro, chloro, bromo, iodo, $C_1$–$C_6$ alkoxy, formyl, amino, NH($C_1$–$C_6$ alkyl), N($C_1$–$C_6$ alkyl)($C_1$–$C_2$ alkyl), SO$_n$($C_1$–$C_6$ alkyl), wherein n is 0, 1 or 2, cyano, carboxy, or amido, wherein said $C_1$–$C_6$ alkyls may be substituted by one hydroxy, trifluoromethyl, amino, carboxy, amido,

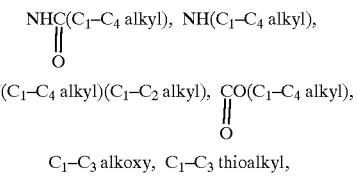

fluoro, bromo, chloro, iodo, cyano or nitro;
R$_{11}$ is hydrogen, hydroxy, fluoro, chloro, COO($C_1$–$C_2$ alkyl), cyano, or CO($C_1$–$C_2$ alkyl); and
R$_{12}$ is hydrogen or $C_1$–$C_4$ alkyl; with the proviso that (1) B is not straight chain $C_1$–$C_{12}$ alkyl, (2) when R$_5$ is unsubstituted cycloakyl, R$_3$ and R$_4$ are hydrogen, and R$_6$ is hydrogen or methyl, then B is not NHR$_2$ wherein R$_2$ is benzyl or thienylmethyl, and (3) when R$_5$ is p-bromophenyl, and R$_3$, R$_4$ and R. are methyl, then B not methylamino or hydroxyethylamino, said disorders being selected from group consisting of panic, phobias including agoraphobia, social phobia, and simple phobia, obsessive-compulsive disorder, post-traumatic stress disorder, single episode depression, recurrent depression, dysthymia, bipolar disorders, cyclothymia, mood disorders, postpartum depression, child abuse induced depression, sleep disorders, stress induced pain perception including fibromyalgia, fibromyalgic sleep disorders, rheumatoid arthritis, osteroarthritis, psoriasis, euthyroid sick syndrome, syndrome of inappropriate antidiarrhetic syndrome hormone (ADH), bulimia nervosa eating disorder, and obesity.

More specific compounds of formula I of the invention include those wherein Y is phenyl substituted by three substituents one each at positions 2, 4 and 6, e.g. 2,4,6-trichlorophenyl, 2,6-dichloro-4-trifluoromethylphenyl, or 2,6-dichloro-4-fluorophenyl. Other more specific compounds of formula I include those wherein XR$_3$ is ethyl or methylthio, those wherein R$_1$ and R$_2$ are each methyl, and those wherein Z is NR$_7$R. and R$_7$is phenyl or phenyl substituted by one of fluoro, chloro, nitro, methyl or methoxy and R$_8$ is as defined above, preferably, (CH$_2$)$_3$OH, CH$_2$CH$_2$OH or methyl.

Preferred compounds of formula I are those wherein Z is 1,2,3,4-tetrahydroisoquinolin-2-yl substituted by R$_5$ which is —(CH$_2$)$_o$—X$_2$-(CH$_2$)$_r$—Q$_2$—R$_6$, more specifically R$_5$ is —(CH$_2$)$_k$OH wherein k is an integer of 1 to 4, or —CH$_2$OCH$_2$CH$_2$OR$_6$. Other preferred compounds of formula I are those wherein Z is 1,2,3,4-tetrahydroquinolin-2-yl wherein R$_5$ is substituted at position 3, and the absolute configuration at the 3 position is either S or R or R,S.

Preferred compounds of the formula I include those wherein Z is as defined in above subparagraph (h); and those wherein Z is as defined in (h), A is linked to position 1, F, G, H, I, J and K are each carbon, and R$_{14}$ is methoxy, ethoxy, isopropoxy, or cyclopropylmethoxy at position 2.

Other preferred compounds of formula I are those wherein Z is as defined in above subparagraph (h), A is linked to position 1, K is nitrogen, F, G, H, I, and J are each carbon, and R$_{14}$ is —X$_2$—(CH$_2$)$_r$Q$_2$R$_6$ at position 2; those wherein Z is as defined in (h), A is linked to position 1, K is nitrogen, F, G, H, I, and J are each carbon, and $R_{14}$ is methoxy, ethoxy, isopropoxy, or cyclopropylmethoxy at position 2; and those wherein Z is as defined in (h), A is at position 1, and $R_{14}$ is ethoxy, isopropoxy or cyclopropylmethoxy at position 2. In these preferred compounds of formula I wherein Z is as defined in (h), $R_{12}$ and $R_{13}$ are preferably hydrogen.

Other preferred compounds of formula I are those wherein Z is as defined in subparagraph (a), B is phenyl, p and m are each 1, and $R_5$ is $CH_2OCH_3$.

Preferred compounds of formula I include those wherein Z is

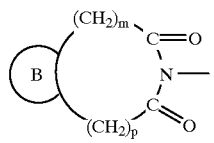

wherein B is phenyl, m is 0, and p is 1.

More specific compounds of the formula VII include those wherein $R_3$ is phenyl substituted independently with one or two of fluoro, chloro, bromo, methyl, trifluoromethyl, nitro, $C_1$–C alkyl, $C_1$–$C_6$ alkyloxy, $SO_2NH_2$, $SO_2NH(C_1$–$C_6$ alkyl), $SO_2N(C_1$–$C_6$ alkyl)$_2$, or $R_3$ is primary, secondary or tertiary alkyl of from 4–9 carbon atoms wherein said $C_4$–$C_9$ alkyl may contain from one to two double or triple bonds and may be substituted by from 1 to 3 substituents $R_6$ which is hydroxy, amino, $C_1$–$C_3$ alkoxy, dimethylamino, diethylamino, methylamino, ethylamino, $NH(C=O)CH_3$, fluoro, chloro, bromo, or $C_1$–$C_3$ thioalkyl.

More specific compounds of the formula VII are those wherein A is C=O, those wherein $R_1$ is amino, methylamino or dimethylamino; those wherein $R_2$ is ethyl or ethylthio and those wherein $R_4$ is 2,4,6-trichlorophenyl, 2,4,6-trimethylphenyl, 2,6-dichloro-4-trifluoromethylphenyl or 4-bromo-2,6-dimethylphenyl.

More specific compounds of formula VII further include those wherein $R_3$ is phenyl which may be substituted at positions 2 or 5 with one or two of methyl, $C_2$–$C_6$ straight-chain or branched alkyl, trifluoromethyl, fluoro, chloro, bromo or nitro, those wherein A and $R_1$ together form a pyrimidine ring, such that the bicyclic structure formed is pyrazolo[3,4-d]pyrimidine, and $R_5$ is substituted at the 6 position; and those wherein $R_3$ is phenyl substituted independently with one or two of fluoro, chloro, bromo, methyl, trifluoromethyl, nitro, $C_1$–$C_6$ alkyl, $C_1$–$C_6$ alkyloxy, $SO_2NH_2$, $SO_2NH(C_1$–$C_6$ alkyl), or $SO_2N(C_1$–$C_6$alkyl)$_2$, $R_4$ is 2,4,6-trichlorophenyl, 2,4,6-trimethylphenyl, 2,6-dichloro-4-trifluoromethylphenyl or 4-bromo-2,6-dimethylphenyl, and $R_2$ is methylthio, methyl or ethyl.

More specific compounds of formula VII also include those wherein $R_3$ is phenyl substituted independently with one or two of fluoro, chloro, bromo, methyl, trifluoromethyl, nitro, $C_1$–$C_6$ alkyl, $C_1$–$C_6$ alkyloxy, $SO_2NH_2$, $SO_2NH$ ($C_1$–$C_6$ alkyl), $SO_2N(C_1$–$C_6$ alkyl)$_2$, or $R_3$ is primary, secondary or tertiary alkyl of from 4–9 carbon atoms wherein said $C_4$–$C_6$ alkyl may contain from one to two double or triple bonds and may be substituted by from 1 to 3 substituents $R_6$ which is hydroxy, amino, $C_1$–$C_3$ alkoxy, dimethylamino, diethylamino, methylamino, ethylamino, $NH(C=O)CH_3$, fluoro, chloro, bromo or $C_1$–$C_3$ thioalkyl; $R_4$ is 2,4,6-trichlorophenyl, 2,4,6-trimethylphenyl, 2,6-dichloro-4-trifluoromethylphenyl or 4-bromo-2,6-dimethylphenyl; $R_1$ is amino, methylamino or dimethylamino; and $R_2$ is methylthio or ethyl.

More specific compounds of the formula VII are those wherein A is $NR_1R_2$, $NHCHR_1R_2$, or $OCHR_1R_2$, wherein $R_1$ is $C_1$–$C_6$ alkyl, which may be substituted by one of hydroxy, fluoro or $C_1$–$C_2$ alkoxy, and may contain one double or triple bond, and $R_2$ is benzyl or $C_1$–$C_5$ alkyl which may contain one double or triple bond, wherein said $C_1$–$C_6$ alkyl or the phenyl in said benzyl may be substituted by fluoro, $C_1$–$C_6$ alkyl, or $C_1$–$C_6$ alkoxy; and those wherein A is $CR_1R_2R_{11}$ wherein $R_1$ is $C_1$–$C_6$ alkyl which may be substituted by one $C_1$–$C_6$ alkoxy or hydroxy, $R_2$ is benzyl or $C_1$–$C_6$ alkyl wherein said $C_1$–$C_6$ alkyl or the phenyl in said benzyl may be substituted by one $C_1$–$C_6$ alkyl, $C_1$–$C_6$ alkoxy, fluoro, chloro or bromo, and $R_{11}$ is hydrogen or fluoro.

More specific compounds of the formula VII include those wherein $R_2$ is ($C_1$–$C_4$ alkylene)aryl wherein said aryl is phenyl, thienyl, benzofuranyl, furanyl, benzothienyl, thiazolyl, pyridyl or benzothiazolyl.

More specific compounds of the formula VII further include those wherein $R_2$ is benzyl para-substituted by one of ethyl, t-butyl, methoxy, trifluoromethyl, nitro, fluoro chloro, or methyl.

Other more specific compounds of the formula VII include those wherein $R_2$ is attached through a methylene or ethylene bridge to quinolyl, pyrrolyl, pyrrolidinyl, pyridyl, tetrahydropyranyl, cyclopropyl, piperidinyl, or benzylpiperidinyl.

More specific compounds VII further include those wherein $R_1$ or $R_2$ is $C_1$–$C_6$ alkyl which may be substituted by one of hydroxy, methoxy, ethoxy, chloro, fluoro, OC(O) $CH_3$, OC(O)NHCH$_3$, or C(O)NH$_2$.

Other more specific compounds VII include those wherein $R_2$ is $C_1$–$C_6$ alkyl substituted by two of methoxy or ethoxy, or one of $COOC_2H_5$, methylthio, or phenyl.

Other more specific compounds VII include those wherein A is $NR_1R_2$ or $CHR_1R_2$ in which $R_1$ and $R_2$ are taken together with N or CH to form a 5- or 6-membered ring having one more nitrogen, sulfur, and/or one oxygen, e.g. pyrrolidinyl, pyrrolyl, pyrazolyl, imidazolyl, oxazolyl, thiazolyl, isoxazolyl, thiadiazolyl, oxadiazolyl, pyridyl, pyrazinyl or pyrimidyl.

Other more specific compounds VII includes those wherein A is $NHCHR_1R_2$ or $OCHR_1R_2$ in which $CHR_1R_2$ is a 5- or 6-membered ring which may contain one oxygen or sulfur, e.g. tetrahydrofuranyl, tetrahydrothiafuranyl and cyclopentanyl.

Preferred compounds of the formula IX of the invention are those wherein B is $NR_1R_2$, $NHCHR_1R_2$, or $OCHR_1R_2$, wherein $R_1$ is $C_1$–$C_6$ alkyl, which may be substituted by one of hydroxy, fluoro or $C_1$–$C_2$ alkoxy, and may contain one double or triple bond; those wherein $R_2$ is benzyl or $C_1$–$C_6$ alkyl which may contain one double or triple bond, wherein said $C_1$–$C_6$ alkyl or the phenyl in said benzyl may be substituted by fluoro, $C_1$–$C_6$ alkyl, or $C_1$–$C_6$ alkoxy; those wherein $R_3$ is methyl, ethyl, fluoro, chloro or methoxy; those wherein $R_4$ and $R_6$ are independently hydrogen, methyl, or ethyl; and those wherein $R_5$ is phenyl substituted by two or three substituents, said substituent being independently fluoro, chloro, bromo, iodo, $C_1$–$C_4$ alkoxy, trifluoromethyl, $C_1$–$C_6$ alkyl which may be substituted by one of hydroxy, $C_1$–$C_4$ alkoxy or fluoro and may have one double or triple bond, —($C_1$–$C_4$ alkylene)O($C_1$–$C_2$ alkyl), $C_1$–$C_3$ hydroxyalkyl, hydroxy, formyl, COO($C_1$–$C_2$ alkyl), —($C_1$–$C_2$ alkylene)amino, or —C(O)($C_1$–$C_4$ alkyl).

In specific methods of the invention, said compound is

2-{1-[1-(2,6-dichloro-4-tirfluoromethylphenyl)-5-dimethylamino-3-ethyl-1H-pyrazol-4-ylmethyl]-napthalen-2-yloxy}-ethanol;

enantiomeric [4-(3-methoxymethyl-3,4-dihydro-1H-isoquinolin-2-ylmethyl)-5-methylsulfanyl-2-(2,4,6-trichlorophenyl)-2H-pyrazol-3-yl]-dimethylaminederivedfrom(+)-3-hydroxymethyl-1,2,3,4-tetrahydroisoquinoline;

enantiomeric [2-(2,6-dichloro-4-trifluoromethylphenyl)4-(3-ethoxymethyl-3,4-dihydro-1H-isoquinolin-2-ylmethyl)-5-ethyl-2H-pyrazol-3-yl]-dimethylamine derived from (+)-3-hydroxymethyl-1,2,3,4-tetrahydroisoquinoline;

[2-(2,6-dichloro-44rifluoromethylphenyl)-5-ethyl-6(7-methoxyquinolin-8ylmethyl)-2H-pyrazol-3-yl]-dimethylamine;

[2-(2,6-dichloro-4-trifluoromethylphenyl)4)2-ethoxy-napthalen-1-ylmethyl)-5-ethyl-2H-pyrazol-3-yl]-dimethylamine;

[4-(2-ethoxynapthalen-1-ylmethyl)-5-ethyl-2-(2,4,6-trichlorophenyl)-2H-pyrazol-3-yl]-dimethylamine;

[4-(7-methoxyquinolin-8-ylmethyl)-5-methylsulfanyl-2-(2,4,6-trichlorophenyl)-2H-pyrazol-3-yl]-dimethylamine;

2-{1-[5-dimethlamino-3-methylsulfanyl-1-(2,4,6-trichlorophenyl)-1H-pyrazol-4-ylmethyl]-napthalen-2-yloxy}-ethanol;

enantiomeric [2-(2,6-dichloro-4-trifluoromethlphenyl)-5-ethyl-4-(3-methoxymethyl-3,4-dihydro-1H-isoquinolin-2-ylmethyl)-2H-pyrazol-3-yl]-dimethylamine derived from (+)-3-hydroxymethyl-1,2,3,4-tetrahydroisoquinoline;

[4-(2-cyclopropylmethoxynapthalen-1-ylmethyl)-5-methylsulfanyl-2-(2,4,6-trichlorophenyl)-2H-pyrazol-3-yl]-dimethylamine.

[5amino-1-(2,6-dichloro-4-trifluoromethylphenyl)-3-methylsulfanyl-1H-pyrazol-4-yl]-(2,5-dimethylphenyl)methanone,

[5-amino-1-(2,6-dichloro-4-trifluoromethylphenyl)-3-methylsulfanyl-1H-pyrazol-4-yl]-(2,5-bis-trifluoromethylphenyl)methanone,

[5-amino-1-(2,6-dichloro-4-trifluoromethylphenyl)-3-methylsulfanyl-1H-pyrazol-4-yl]-(5-isopropyl-2-methylphenyl)methanone,

[5-amino-3-methylsulfanyl-1-(2,4,6-trichlorophenyl)-1H-pyrazolyl]-(5-isopropyl-2-methylphenyl)methanone, or

[5-amino-1-(4bromo-2,6-dimethylphenyl)-3-methylsulfanyl-1H-pyrazol-4-yl]-(2,5-dibromophenyl)methanone.

[5-amino-1-(2,6-dichloro-4-trifluoromethylphenyl)-3-methylsulfanyl-1H-pyrazol-4-l]-(2,5-dimethylphenyl)methanone,

[5-amino-1-(2,6-dichloro-4-trifluoromethylphenyl)-3-methylsulfanyl-1H-pyrazol-4-yl]-(2,5-bis-trifluoromethylphenyl)methanone,

[5-amino-1-(2,6-dichloro-4-trfluoromethylphenyl)-3-methylsulfanyl-1H-pyrazol-4-yl]-(5-isopropyl-2-methylphenyl)methanone,

[5-amino-3-methylsulfanyl-1-(2,4,6-trichlorophenyl)-1H-pyrazol-4-yl]-(5-isopropyl-2-methylphenyl)methanone, or

[5-amino-1-(4-bromo-2,6-dimethylphenyl)-3-methylsulfanyl-1H-pyrazol-4-yl]-(2,5-dibromophenyl)methanone;

3-{(4-methyl-benzyl)-[3,6-dimethyl-1-(2,4,6-trimethylphenyl)-1H-pyrazolo [3,4-d]pyrimidin-4-yl]-amino}-propan-1-ol;

diethyl-[6-methyl-3-methylsulfanyl-1-(2,4,6-trichlorophenyl)-1H-pyrazolo[3,4-d]pyrimidin-4-yl]-amine;

2-{butyl-[6-methyl-3-methylsulfanyl-1-(2,4,6-trichlorophenyl)-1H-pyrazolo [3,4-d]pyrimidin-4-yl]-amino}-ethanol;

dibutyl-[6-methyl-3-methylsulfanyl-1-(2,4,6-trichlorophenyl)-1H-pyrazolo[3,4-d]pyrimidin-4-yl}-amine;

butyl-ethyl-[6-methyl-3-methylsulfanyl-1-(2,4,6-trichlorophenyl)-1H-pyrazolo [3,4-d]pyrimidin-4-yl]-amine;

butyl-ethyl-[6-methyl-3-methylsulfanyl-1-(2,4,6-trichlorophenyl)-1H-pyrazolo[3,4-d]pyrimidin-4-yl]-amine;

butyl-cyclopropylmethyl-[6-methyl-3-methylsulfanyl-1-(2,4,6-trichlorophenyl)-1H-pyrazolo[3,4-d]pyrimidin-4-yl]-amine;

di-1-propyl-[6-methyl-3-methylsulfanyl-1-(2,4,6-trichlorophenyl)-1H-pyrazolo[3,4-d]pyrimidin-4-yl]-amine;

diallyl-[6-methyl-3-methylsulfanyl-1-(2,4,6-trichlorophenyl)-1H-pyrazolo[3,4-d]pyrimidin-4-yl]-amine;

butyl-ethyl-[6-chloro-3-methylsulfanyl-1-(2,4,6-trichlorophenyl)-1H-pyrazolo [3,4-d]pyrimidin-4-yl]-amine;

butyl-ethyl-[6-methoxy-3-methylsulfanyl-1-(2,4,6-trichlorophenyl)-1H-pyrazolo[3,4-d]pyrimidin-4-yl]-amine;

propyl-ethyl-[3,6-dimethyl-1-(2,4,6-trimethylphenyl)-1H-pyrazolo[3,4-d]pyrimidin-4-yl]-amine;

4-(1-ethyl-propyl)-6-methyl-3-methylsulfanyl-1-(2,4,6-trimethylphenyl)-1H-pyrazolo[3,4-d]pyrimidine.

n-butyl-thyl-[2,5-dimethyl-7-(2,4,6-trimethylphenyl)-7H-pyrrolo [2,3-d]pyrimidin-4-yl]amine;

di-n-propyl-[2,5-dimethyl-7-(2,4,6-trimethylphenyl)-7H-pyrrolo [2,3-d]pyrimidin-4-yl]amine;

ethyl-n-propyl-[2,5-dimethyl-7-(2,4,6-trimethylphenyl)-7H-pyrrolo[2,3-d]pyrimidin-4-l]amine;

diethyl-2,5-dimethyl-7-(2,4,6-trimethylphenyl)-7H-pyrrolo[2,3-d]imidin-4-yl]amine;

n-butyl-ethyl-[2,5,6-trimethyl-7-(2,4,6-trimethylphenyl)-7H-pyrrolo [2,3-d]pyrimidin-4-yl]amine;

2-{N-n-butyl-N-[2,5-dimethyl-7-(2,4,6-trimethylphenyl)-7H-pyrrolo[2,3-d]pyrimidin-4-yl]amino}-ethanol;

4-(1-ethyl-propyl)-2,5,6-trimethyl-7-(2,4,6-trimethylphenyl)-7H-pyrrolo [2,3-d]pyrimidine;

n-butyl-ethyl-[2,5-dimethyl-7-(2,4-dimethylphenyl)-7H-pyrrolo [2,3-d]pyrimidin-4-yl]amine;

2,5-dimethyl-7-(2,4,6-trimethylphenyl)-7H-pyrrolo [2,3-d]pyrimidyl-4-yl]-(1-ethyl-propyl)amine; or 2-[7-(4-bromo-2,6-dimethylphenyl)-2,5-dimethyl-7H-pyrrolo [2,3-d] pyrimidin-4-ylamino]-butan-1-ol.

DETAILED DESCRIPTION OF THE INVENTION

Whenever reference herein is made to groups $(CH_2)_q Q_1 R_{19}$ and $(CH_2)_0-X_2-CH_2)_r-Q_2-R_6$, then $X_1$ and $Q_1$, and $X_2$ and $Q_2$, respectively, are not both a heteroatom when q or r, respectively, is 1.

Whenever one of the substituents, e.g. Y or $R_1$ in formula 1, is a heterocyclic group, the attachment of the group is through a carbon atom.

Whenever reference is made herein to alkyl, a straight and branched chain alkyl of one to six carbon atoms is included, such as methyl, ethyl, isopropyl or hexyl.

Whenever reference is made herein to $C_1$–$C_6$ alkyl, in the definition of $R_5$ and $R_1$ formula VII, this includes unsaturated $C_2$–$C_6$ alkyl, such as $C_2$–$C_6$ alkyl having one double or triple bond, $C_3$–$C_6$ alkyl having two double bonds, and $C_4$–$C_6$ alkyl having two triple bonds.

Whenever reference is made herein to 3- to 8-membered cycloalkyl or 9- to 12-membered bicycloalkyl containing one to three of O, S or N—Z, it is understood that the oxygen and sulfur ring atoms are not adjacent to each other. The three membered cycloalkyl has just one O, S or N—Z. An example of a six membered cycloalkyl having O and N is morpholinyl.

Whenever reference is made herein to $C_1$–$C_4$ alkyl or $C_1$–$C_6$ alkyl which "may contain one or two double or triple bonds" in the definitions of $R_1$, $R_2$ and $R_3$, it is understood that at least two carbons are present in the alkyl for one double or triple bond, and at least four carbons for two double and triple bonds.

Whenever an alkoxy group, e.g. in the definitions of $R_1$ and $R_2$ in formula VIII, may have a double or triple bond, it is understood that such double or triple bond is not directly attached to the oxygen.

The compounds of formulae I, VII, VIII and IX, their pharmaceutically acceptable salts, and their preparation are described in, respectively, patent applications PCT/US93/10716, PCT/US93/10539, PCT/US93/11333, and PCT/US93/10715. The compounds of formulae I, VII, VIII and IX, and their pharmaceutically acceptable salts are designated hereafter as "the active compound". It is noted that the active compounds are described above substantially in accordance with the respective patent applications.

The acid addition salts are prepared in a conventional manner by treating a solution or suspension of the free base of the active compound with one chemical equivalent of a pharmaceutically acceptable acid. Conventional concentration or crystallization techniques are employed in isolating the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids.

The active compounds may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining the active compounds and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the active compound in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The effective dosage for the active compound depends on the intended route of administration and other factors such as age and weight of the patient, as generally known to a physician. The dosage also depends on the illness to be treated. The daily dosage will generally range from about 0.1 to 50 mg/kg of the body weight of the patient to be treated. The daily dosage may be given in a single dose or up to three divided doses.

The methods for testing the active compounds for their CRF antagonist activity are as described in Endocrinology, 116, 1653–1659 (1985) and Peptides 10, 179–188 (1989) which determine the binding affinity of a test compound for a CRF receptor. The binding affinities for the active compounds, expressed as $IC_{50}$ values, generally range from about 0.2 namomolar to about 10 micromolar.

What is claimed is:

1. A method for the treatment of certain disorders, which comprises administering to a subject in need of such treatment an effective amount of a compound of the formula (A)

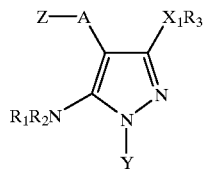

or a pharmaceutically acceptable acid addition salt thereof, wherein A is $CH_2$;

$R_1$, $R_2$ and $R_3$ are each independently linear $C_1$–$C_6$ alkyl, branched $C_3$–$C_8$ alkyl, $C_3$–$C_8$ alkenyl wherein the double bond is not adjacent to the N or $X_1$ when $X_1$ is oxygen or sulfur, or $C_3$–$C_7$ cycloalkyl $(CH_2)_n$ wherein n is 0, 1, 2, 3 or 4; or $R_1$ and $R_2$ when taken together with the nitrogen form a saturated four, five or six membered ring optionally condensed with benzo; and $R_3$ may also be $(CH_2)_q Q_1 R_{19}$ wherein q is 0, 1 or 2, $Q_1$ is O, S, NH, N($C_1$–$C_6$ alkyl) or a covalent bond when $X_1$ is not a covalent bond, and $R_{19}$ is hydrogen, linear $C_1$–$C_6$ alkyl, branched $C_3$–$C_8$ alkyl, $C_3$–$C_8$ alkenyl, $C_3$–$C_8$ cycloalkyl or $C_3$–$C_6$ cycloalkyl $(CH_2)$, wherein n is 1 to 4;

$X_1$ is a covalent bond, $CH_2$, NR wherein R is hydrogen or linear $C_1$–$C_6$ alkyl, O, or S;

Y is phenyl, thienyl, benzothienyl, pyridyl, quinolyl, pyrazinolyl, pyrimidyl, imidazolyl, benzimidazolyl, furanyl, benzofuranyl, thiazolyl, benzothiazolyl, isothiazolyl, benzisothiazolyl, isoxazolyl, benzisoxazolyl, triazolyl, pyrazolyl, pyrrolyl, indolyl, azaindolyl, oxazolyl, benzoxazolyl, pyrrolidinyl, thiazolidinyl, morpholinyl, or piperidinyl, each of which may be substituted by one to three of any one of fluoro, chloro, bromo, or methyl, or one of trifluoromethyl; with the proviso that Y is not unsubstituted phenyl; and Z is (a)

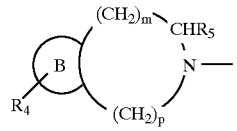

II wherein the B ring is phenyl, naphthyl, pyridyl, pyrimidinyl, pyrazinyl, pyridazinyl, triazilyl, pyrrolyl, pyrazolyl, imidazolyl, triazolyl, thienyl, or indolyl, each of which may be substituted by methyl, methoxy, fluoro, chloro, bromo or iodo; or a saturated 5- or 6-membered carbocyclic ring or a partially unsaturated ring having one or two double bonds;

$R_4$ is hydrogen, $C_1$–$C_6$ alkyl, $C_1$–$C_6$ alkoxy, or hydroxy, fluoro, chloro, bromo, iodo, or trifluoromethyl;

$R_5$ is hydrogen, linear $C_1$–$C_6$ alkyl, branched $C_3$–$C_8$ alkyl, $C_3$–$C_8$ alkenyl, or $(CH_2)_o$—$X_2$—$(CH_2)_r$—$Q_2$—$R_6$;

$R_6$ is hydrogen, linear $C_1$–$C_6$ alkyl, branched $C_3$–$C_8$ alkyl, or $C_3$–$C_8$ alkenyl;

$X_2$ and $Q_2$ are each independently O, S, NH, N($C_1$–$C_6$ alkyl), or one of $X_2$ and Q may be a covalent bond;

m is 0 or 1;
o is 1 or 2;
p is 1 or 2;
r is 0, 1, or 2;

(b)

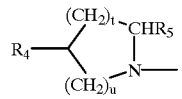

III wherein $R_4$ and $R_5$ are as defined above, and t and u are each independently 1 or 2;

(c) —$NR_7R_8$ wherein $R_7$ and $R_8$ are each independently hydrogen, $C_1$–$C_6$ linear alkyl, branched $C_3$–$C_8$ alkyl, $C_3$–$C_8$ alkenyl, $(CH_2)_v CH_2OH$, $(CH_2)_v NR_9R_{10}$, wherein v is 0 to 3, and $R_9$ and $R_{10}$ are each independently hydrogen, or linear $C_1$–$C_6$ alkyl; $C_1$–$C_{12}$ cycloalkyl, $(C_3$–$C_{12}$ cycloalkyl) $(CH_2)_n$, $(C_6$–$C_{10}$ bicycloalkyl) $(CH_2)_n$, wherein n is 0 to 4, benzofused $C_3$–$C_6$ cycloalkyl, $C_1$–$C_6$ hydroxyalkyl, phenyl, phenyl $(C_1$–$C_3$ alkylene), each of which may be substituted by one or two of hydroxy, fluoro, chloro, bromo, $C_1$–$C_5$ alkyl, or $C_1$–$C_5$ alkoxy; or $R_7$ and $R_8$ may be taken together with the nitrogen to form a saturated or partially unsaturated 5- to 7-membered ring which may contain one of O, S, NH or N($C_1$–$C_6$ alkyl) and which may be substituted by $C_1$–$C_6$ alkyl, hydroxy or phenyl wherein any double bond(s) are not adjacent to any heteroatoms;

(e)

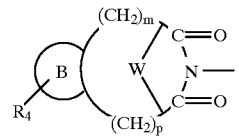

V wherein B, $R_4$, m and p are as defined above;

(f)

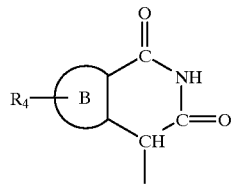

VI wherein B and R4 are as defined above;

(g) $O(CH_2)_v R_{11}$ wherein v is 0 to 3 and $R_{11}$ is linear $C_1$–$C_6$ alkyl, branched $C_3$–$C_8$ alkyl, phenyl, naphthyl, 1,2,3,4-tetrahydronaphthyl, thienyl, benzothienyl, pyridyl, quinolyl, pyrazinolyl, pyrimidyl, imidazolyl, benzimidazolyl, furanyl, benzofuranyl, thiazolyl, benzothiazolyl, isothiazolyl, benzisothiazolyl, isoxazolyl, benzisoxazolyl, triazolyl, pyrazolyl, pyrrolyl, indolyl, azaindolyl, oxazolyl, benzoxazolyl, pyrrolidinyl, thiazolidinyl, morpholinyl, piperidinyl, or thienyl, each of which may be substituted by one or two of any one of fluoro, chloro, bromo, methyl, or trifluoromethyl;

(B)

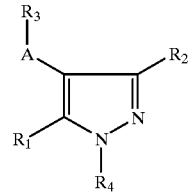

VII or a pharmaceutically acceptable acid addition salt thereof, wherein

A is C=O or $SO_2$, or A and $R_1$ together with the carbons to which they are attached form pyrimidinyl or 5-pyridyl which may be substituted by $R_5$ which is hydrogen, $C_1$–$C_6$ alkyl, fluoro, chloro, bromo, hydroxy, amino, $O(C_1$–$C_6$ alkyl), $NH(C_1$–$C_6$ alkyl), $N(C_1$–$C_6$ alkyl)($C_1$–$C_6$ alkyl), SH, $S(O)_n(C_1$–$C_6$ alkyl) wherein n 0, 1 or 2, wherein said $C_1$–$C_6$ alkyl may be substituted by from 1 to 3 substituents $R_6$ which is hydroxy, amino, $C_1$–$C_3$ alkoxy, dimethylamino, diethylamino, methylamino, ethylamino, NH(C=O)$CH_3$, fluoro, chloro, bromo or $C_1$–$C_3$ thioalkyl;

$R_1$ is hydrogen, $C_1$–$C_6$ alkyl, amino, $O(C_1$–$C_6$ alkyl), $NH(C_1$–$C_6$ alkyl), $N(C_1$–$C_6$ alkyl)($C_1$–$C_6$ alkyl), wherein said $C_1$–$C_6$ alkyl may be substituted by from 1 to 3 substituents $R_6$ as defined above;

$R_2$ is hydrogen, $C_1$–$C_6$ alkyl, hydroxy, amino, $O(C_1$–$C_6$ alkyl), $NH(C_1$–$C_6$ alkyl), $N(C_1$–$C_6$ alkyl)($C_1$–$C_6$ alkyl), SH, S(O)$_n$(C$_1$–C$_6$ alkyl) wherein n=0, 1, or 2, cyano, hydroxy, carboxy, or amido, wherein said alkyls may be substituted by one to three of hydroxy, amino, carboxy, amido, NH(C=O)(C$_1$–C$_6$ alkyl), N(C$_1$–C$_6$ alkyl)(C$_1$–C$_6$ alkyl), (C=O)O(C$_1$–C$_6$ alkyl), C$_1$–C$_3$ alkoxy, C$_1$–C$_3$ thioalkyl, fluoro, bromo, chloro, iodo, cyano or nitro;

R$_3$ is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, pyridinyl, tetrazolyl, or 9to 12 membered bicycloalkyl, optionally containing one to three of O, S or N—Z wherein Z is hydrogen, C$_1$–C$_4$ alkyl, C$_1$–C$_4$ alkanoyl, phenyl or phenylmethyl, wherein each one of the above groups may be substituted independently by from one to three of fluoro, chloro, bromo, C$_1$–C$_6$ alkyl, C$_1$–C$_6$ alkoxy, or trifluoromethyl, or one of cyano, nitro, amino, NH(C$_1$–C$_6$ alkyl), N(C$_1$–C$_4$ alkyl)(C$_1$–C$_2$ alkyl), COO(C$_1$–C$_4$ alkyl), CO(C$_1$–C$_4$ alkyl), SO$_2$NH(C$_1$–C$_4$ alkyl), SO$_2$N(C$_1$–C$_4$ alkyl)(C$_1$–C$_2$ alkyl), SO$_2$NH$_2$, NHSO$_2$(C$_1$–C$_4$ alkyl), S(C$_1$–C$_6$ alkyl), SO$_2$(C$_1$–C$_6$ alkyl), wherein said C$_1$–C$_4$ alkyl and C$_1$–C$_6$ alkyl may be substituted by one or two of fluoro, chloro, hydroxy, amino, methylamino, dimethylamino or acetyl; and R$_4$ is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, pyridinyl, tetrazolyl, or 3 to 8-membered cycloalkyl or 9 to 12-membered bicycloalkyl, optionally containing one to three of O, S or N—Z wherein Z is hydrogen, C$_1$–C$_4$ alkyl, C$_1$–C$_4$ alkanoyl, phenyl or phenylmethyl, wherein each of the above groups may be substituted independently by from one to three of fluoro, chloro, bromo, trifluoromethyl, C$_1$–C$_6$ alkyl or C$_1$–C$_6$ alkoxy, or one of cyano, nitro, amino, NH(C$_1$–C$_6$ alkyl), N(C$_1$–C$_4$ alkyl)(C$_1$–C$_2$ alkyl), COO(C$_1$–C$_4$ alkyl), CO(C$_1$–C$_4$ alkyl), SO$_2$NH(C$_1$–C$_4$ alkyl), SO$_2$N(C$_1$–C$_4$ alkyl)(C$_1$–C$_2$ alkyl), SO$_2$NH$_2$, NH$_2$SO$_2$(C$_1$–C$_4$ alkyl), S(C$_1$–C$_6$ alkyl), SO$_2$(C$_1$–C$_6$ alkyl), wherein said C$_1$–C$_4$ alkyl and C$_1$–C$_6$ alkyl may be substituted by one or two of fluoro, chloro, hydroxy, amino, methylamino, dimethylamino or acetyl; provided that (1) R$_4$ is not unsubstituted phenyl; (2) when R$_1$ is amino, R$_2$ is methylthio, R$_4$ is 2,4,6-trichlorophenyl, and A is C=O, then R$_3$ is not 2-chlorophenyl; and (3) R$_1$ and R$_2$ are not both hydrogen; or (C)

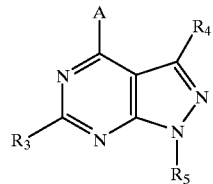

VIII or a pharmaceutically acceptable acid addition salt thereof, wherein

A is NR$_1$R$_2$, CR$_1$R$_2$R$_{11}$, or C(=CR$_1$R$_{12}$)R$_2$, NHCR$_1$R$_2$R$_{11}$, OCR$_1$R$_2$R$_{11}$, SCR$_1$R$_2$R$_{11}$, NHNR$_1$R$_2$, CR$_2$R$_{11}$ NHR$_1$, CR$_2$R$_{11}$ OR$_1$, CR$_2$R$_{11}$SR$_1$ or C(O)R$_2$;

R$_1$ is hydrogen, or C$_1$–C$_6$ alkyl which may be substituted by one or two substituents R$_6$ independently selected from the group consisting of hydroxy, fluoro, chloro, bromo, iodo, C$_1$–C$_6$ alkoxy, —OC(O)(C$_1$–C$_6$ alkyl), —OC(O)N(C$_1$–C$_4$ alkyl)(C$_1$–C$_2$ alkyl),amino, NH(C$_1$–C$_4$ alkyl), N(C$_1$–C$_2$ alkyl)(C$_1$–C$_4$ alkyl), S(C$_1$–C$_6$ alkyl), OC(O)NH(C$_1$–C$_4$ alkyl), N(C$_1$–C$_2$ alkyl)C(O)(C$_1$–C$_4$ alkyl), —NHC(O)(C$_1$–C$_4$ alkyl), COOH, —C(O)O(C$_1$–C$_4$ alkyl), —C(O)NH(C$_1$–C$_4$ alkyl), —C(O)N(C$_1$–C$_4$ alkyl)(C$_1$–C$_2$ alkyl), SH, CN, NO$_2$, SO(C$_1$–C$_4$ alkyl), SO$_2$(C$_1$–C$_4$ alkyl), SO$_2$NH(C$_1$–C$_4$ alkyl), SO$_2$N(C$_1$–C$_4$ alkyl)(C$_1$–C$_2$ alkyl), and said C$_1$–C$_6$ alkyl may contain one or two double or triple bonds;

R$^2$ is C$_1$–C$_{12}$ alkyl, aryl or (C$_1$–C$_{10}$ alkylene)aryl wherein said aryl is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, azaindolyl, oxazolyl, or benzoxazolyl; 3- to 8-membered cycloalkyl or (C$_1$–C$_6$ alkylene) cycloalkyl, wherein said cycloalkyl may contain one or two of O, S or N—Z wherein Z is hydrogen, C$_1$–C$_4$ alkyl, benzyl or C$_1$–C$_4$ alkanoyl, wherein R$^2$ may be substituted independently by from one to three of chloro, fluoro, or C$_1$–C$_4$ alkyl, or one of hydroxy, bromo, iodo, C$_1$–C$_6$ alkoxy, —OC(O)(C$_1$–C$_6$ alkyl), O—C—N(C$_1$–C$_4$ alkyl)(C$_1$–C$_2$ alkyl), S(C$_1$–C$_6$ alkyl), NH$_2$, NH(C$_1$–C$_2$ alkyl), N(C$_1$–C$_2$ alkyl) (C$_1$–C$_4$ alkyl), N(C$_1$–C$_4$ alkyl)—C(O)(C$_1$–C$_4$ alkyl), NHC(O)(C$_1$–C$_4$ alkyl), COOH, C(O)O(C$_1$–C$_4$ alkyl), C(O)NH(C$_1$–C$_4$ alkyl), C(O)N(C$_1$–C$_4$ alkyl)(C$_1$–C$_2$ alkyl), SH, CN, NO$_2$, SO(C$_1$–C$_4$ alkyl), SO$_2$(C$_1$–C$_4$ alkyl), SO$_2$NH (C$_1$–C$_4$ alkyl), SO$_2$N(C$_1$–C$_4$ alkyl)(C$_1$–C$_2$ alkyl), and wherein said C$_1$–C$_{12}$ alkyl or C$_1$–C$_{10}$ alkylene may contain one to three double or triple bonds; or NR$_1$R$_2$ or CR,R$_2$R$_{11}$ may form a 4- to 8-membered ring optionally containing one or two double bonds or one or two of O, S or N—Z wherein Z is hydrogen, C$_1$–C$_4$ alkyl, benzyl, or C$_1$–C$_4$ alkanoyl;

R$_3$ is hydrogen, C$_1$–CC alkyl, fluoro, chloro, bromo, iodo, hydroxy, amino, O(C$_1$–C$_6$ alkyl), NH(C$_1$–CC alkyl), N(C$_1$–C$_4$ alkyl)(C$_1$–C$_2$ alkyl), SH, S(C$_1$–C$_4$ alkyl), SO(C$_1$–C$_4$ alkyl), or SO$_2$(C$_1$–C$_4$ alkyl), wherein said C$_1$–C$_4$ alkyl and C$_1$–C$_6$ alkyl may contain one or two double or triple bonds and may be substituted by from 1 to 3 substituents R$_7$ independently selected from the group consisting of hydroxy, amino, C$_1$–C$_3$ alkoxy, dimethylamino, diethylamino, methylamino, ethylamino, NHC(O)CH$_3$, fluoro, chloro or C$_1$–C$_3$ thioalkyl;

R$_4$ is hydrogen, C$_1$–C$_6$ alkyl, fluoro, chloro, bromo, iodo, C$_1$–C$_6$ alkoxy, amino, NH(C$_1$–C$_6$ alkyl), N(C$_1$–C$_6$ alkyl) (C$_1$–C$_2$ alkyl), SO$_n$(C$_1$–C$_6$ alkyl), wherein n is 0, 1 or 2, cyano, hydroxy, carboxy, or amido, wherein said C$_1$–C$_6$ alkyls may be substituted by one to three of hydroxy, amino, carboxy, amido, NHC(O)(C$_1$–C$_4$ alkyl), NH(C$_1$–C$_4$ alkyl), N(C$_1$–C$_4$ alkyl)(C$_1$–C$_2$ alkyl), —C(O)O(C$_1$–C$_4$ alkyl), C$_1$–C$_3$ alkoxy, C$_1$–C$_3$ thioalkyl, fluoro, bromo, chloro, iodo, cyano or nitro;

R$_5$ is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, pyrrolopyridyl benzoxazolyl, oxazolyl, pyrrolidinyl, thiazolidinyl, piperazinyl, piperidinyl, tetrazolyl, or 3- to 8-membered cycloalkyl or 9- to 12-membered bicycloalkyl, optionally containing one or two of O, S or N—Z wherein Z is hydrogen, $C_1$–$C_4$ alkyl, $C_1$–$C_4$ alkanoyl, phenyl or benzyl, wherein each one of the above groups may be substituted independently by from one to three of fluoro, chloro, bromo, formyl, $C_1$–$C_6$ alkyl, $C_1$–$C_6$ alkoxy or trifluoromethyl, or one of hydroxy, iodo, cyano, nitro, amino, cyclopropyl, NH($C_1$–$C_4$ alkyl), N($C_1$–$C_4$ alkyl)($C_1$–$C_2$ alkyl), COO($C_1$–$C_4$ alkyl), CO($C_1$–$C_4$ alkyl), $SO_2$NH($C_1$–$C_4$ alkyl), $SO_2$N($C_1$–$C_4$ alkyl)($C_1$–$C_2$ alkyl), $SO_2NH_2$, $NHSO_2$($C_1$–$C_4$ alkyl), S($C_1$–$C_6$ alkyl), $SO_2$($C_1$–$C_6$ alkyl), wherein said $C_1$–$C_4$ alkyl and $C_1$–$C_6$ alkyl may have one double or triple bond and may be substituted by one or two of fluoro, chloro, hydroxy, amino, methylamino, dimethylamino or acetyl; with the proviso that $R_5$ is not unsubstituted phenyl;

$R_{11}$ is hydrogen, hydroxy, fluoro, chloro, COO($C_1$–$C_2$ alkyl), cyano, or CO($C_1$–$C_2$ aklyl); and $R_{12}$ is hydrogen or $C_1$–$C_4$ alkyl;

(a) A is not straight chain $C_1$–$C_{12}$ alkyl;

(b) $R_5$ is not a sugar group;

(c) when $R_3$ and $R_4$ are hydrogen and R. is chlorophenyl, then A is not NH—CH($CH_3$)—($CH_2$)$_3$—N($C_2H_5$)$_2$;

(d) when $R_3$ and $R_4$ are hydrogen and A is $NR_1R_2$ wherein R, is $C_3$–$C_7$ cycloalkyl, and $R_2$ is $C_2$–C, alkenyl, phenyl-($C_1$–$C_6$ alkylene) or hetero-($C_1$–$C_6$ alkylene) wherein the hetero radical is furyl, thienyl or pyridinyl, and wherein said phenyl may be substituted by fluoro, chloro, bromo or iodo, then $R_5$ is not tetrahydrofuranyl or tetrahydropyranyl;

(e) when $R_3$ is methoxy, methylthio, or methylsulfonyl, $R_4$ is hydrogen, and $R_5$ is tetrahydrofuranyl or tetrahydropyranyl, then A is not NH($C_1$–$C_2$alkyl), morpholinyl, hydrazino, or $NHC_2H_4C_6H_5$ which may be substituted by one methyl or two methoxy;

(f) when $R_3$ is hydrogen, $C_1$–$C_6$ alkyl, hydrazino, chloro, bromo, SH, or S ($C_1$–$C_4$ alkyl), $R_4$is hydrogen and $R_5$ is $C_3$–$C_8$ cycloalkyl, then A is not hydrazino, NH($C_1$–$C_2$ alkyl) or N($C_1$–$C_6$ alkyl) ($C_1$–$C_{12}$ alkyl);

(g) when $R_3$ and $R_4$ are hydrogen and A is NH($CH_2$)$_m$ COOH wherein m is 1–12, then $R_5$ is not phenyl substituted by one of fluoro, chloro, bromo or iodo;

(h) when $R_3$ is hydrogen, hydroxy, methylthio, chloro or NHbenzyl, $R_4$ is hydrogen, and $R_5$ is chlorophenyl or bromophenyl, then A is not NH($C_1$–$C_{12}$ alkyl), NHallyl, or N($C_1$–$C_6$ alkyl) ($C_1$–$C_{12}$ alkyl), wherein said $C_1$–$C_{12}$ alkyl may be substituted by $NC_2H_5$, or NH benzyl which may be substituted by one or two bromo, chloro, fluoro, $NC_2H_5$ phenyl or morpholinopropyl;

(i) when $R_3$ and $R_4$ are hydrogen and $R_5$ is nitrophenyl, then A is not $NHR_2$ wherein $R_2$ is $C_1$–$C_{12}$ alkyl which may be substituted by two hydroxy, or $R_2$ is phenyl or benzyl;

(j) when $R_3$ is chloro or O($C_1$–$C_6$ alkyl), $R_4$ is hydrogen, and A is $NHR_2$ wherein $R_2$ and $R_2$ are independently hydrogen or $C_1$–$C_6$ alkyl, then $R_5$ is not chlorophenyl; and (k) when $R_3$ is hydrogen, A is benzyl or phenethyl, and $R_4$is fluoro, chloro, bromo or iodo, then $R_5$ is not 5'-deoxy-ribofuranosyl or 5'-amino-5'-deoxy-ribofuranosyl; phobias obsessive-compulsive disorder, post-traumatic stress disorder, single episode depression, recurrent depression, dysthymia, bipolar disorders, cyclothymia, mood disorders, postpartum depression, child abuse induced depression, sleep disorders, stress induced pain perception fibromyalgic sleep disorders, rheumatoid arthritis, osteroarthritis, psoriasis, euthyroid sick syndrome, syndrome of inappropriate antidiarrhetic syndrome hormone (ADH), bulimia nervosa eating disorder, and obesity.

2. A method according to claim 1, wherein said compound is

2-{1-[1-(2,6-dichloro-4-tirfluoromethylphenyl)-5dimethylamino-ethyl-1H-pyrazol-4-ylmethyl]-napthalen-2-yloxy}-ethanol;

enantiomeric [4-(3-methoxymethyl-3,4-dihydro-1H-isoquinolin-2-ylmethyl)-5-methylsulfanyl-2-(2,4,6-trichlorophenyl)-2H-pyrazol-3-y-]-dimethylamine derived from (+)-3-hydroxymethyl-1,2,3,4-tetrahydroisoquinoline;

enantiomeric [2-(2,6-dichloro-4-trifluoromethylphenyl)4-(3-ethoxymethyl-3,4-dihydro-1H-isoquinolin-2-ylmethyl)-5-ethyl-2H-pyrazol-3-yl]-dimethylamine derived from (+)-3-hydroxymethyl-1,2,3,4-tetrahydroisoquinoline;

[2-(22,6-dichloro-4-trfluoromethylphenyl)-5-ethyl-2(7-methoxyquinolin-ylmethyl)-2H-pyrazol-3-yl]-dimethylamine;

[2-(2,6-dichloro-4-trifluoromethylphenyl)-4-)2-ethoxy-napthalen-1-ylmethyl)-ethyl-2H-pyrazol-3-yl]-dimethylamine;

[4(2-thoxynapthalen-1-ylmethyl)-5-ethyl-2-(2,4,6-trichlorophenyl)-2H-pyrazol-3-yl]-dimethylamine;

[4(7-methoxyquinolin-8-ylmethyl)-5-methylsulfanyl-2-(2,4,6-trichlorophenyl)-2H-pyrazol-3-yl]-dimethylamine;

2-{1-[5-dimethlamino-3-methylsulfanyl-1-(2,4,6-trichlorophenyl)-1H-pyrazol-4-ylmethyl]-napthalen-2-yloxy}-ethanol;

enantiomeric [2-(2,6-dichloro-4-trifluoromethlphenyl)-5-ethyl-4-(3-methoxymethyl-3,4-dihydro-1H-isoquinolin-2-ylmethyl)-2H-pyrazol-3-yl]-dimethylamine derived from (+)-3-hydroxymethyl-1,2,3,4-tetrahydroisoquinoline; and

[4-(2-cyclopropylmethoxynapthalen-1-ylmethyl)-5-methylsulfanyl-2-(2,4,6-trichlorophenyl)-2H-pyrazol-3-yl]-dimethylamine.

3. A method according to claim 1, wherein said compound is

[5amino-1-(2,6-dichloro-4-trifluoromethylphenyl)-3-methylsulfanyl-1H-pyrazol-4-yl]-(2,5-dimethylphenyl)methanone,

[5-amino-1-(2,6-dichloro-4-trifluoromethylphenyl)-3-methylsulfanyl-1H-pyrazol-4-yl]-(2,5-bis-trifluoromethylphenyl)methanone,

[5-amino-1-(2,6-dichloro-4-trifluoromethylphenyl)-3-methylsulfanyl-1H-pyrazol-4-yl]-(5-isopropyl-2-methylphenyl)methanone,

[5-amino-3-methylsulfanyl-1-(2,4,6-trichlorophenyl)-1H-pyrazol-4-yl]-(5-isopropyl-2-methylphenyl)methanone, or

[5-amino-1-(4-bromo-2,6-dimethylphenyl)-3-methylsulfanyl-1H-pyrazol-4-yl]-(2,5-dibromophenyl)methanone.

4. A method according to claim 1, wherein said compound is

[5-amino-1-(2,6-dichloro-4-trifluoromethylphenyl)-3-methylsulfanyl-1H-pyrazol-4-yl]-(2,5-dimethylphenyl)methanone, [5-amino-1-(2,6-dichloro-4-trifluoromethylphenyl)-3-methylsulfanyl-1H-pyrazol-4-yl]-(2,5-bis-trifluoromethylphenyl)methanone,

[5-amino-1-(2,6-dichloro-4-trifluoromethylphenyl)-3-methylsulfanyl-1H-pyrazol-4-yl]-(5-isopropyl-2-methyl phenyl)methanone,

[5-amino-3-methylsulfanyl-1-(2,4,6-trichlorophenyl)-1H-pyrazolyl]-(5isopropyl-2-methylphenyl)methanone, or

[5-amino-1-(4-bromo-2,6-dimethylphenyl)-3-methylsulfanyl-1H-pyrazol-4-yl]-(2,5-dibromophenyl)methanone.

5. A method according to claim 1 wherein said compound is

3-{(4-methyl-benzyl)-[3,6-dimethyl-1-(2,4,6-trimethylphenyl)-1H-pyrazolo [3,4-d]pyrimidin-4-yl]-amino}-propan-1-ol;

diethyl-[6-methyl-3-methylsulfanyl-1-(2,4,6-trichlorophenyl)-1H-pyrazolo[3,4-d]pyrimidin-4-yl]-amine;

2-{butyl-[6-methyl-3-methylsulfanyl-1-(2,4,6-trichlorophenyl)-1H-pyrazolo [3,4-d]pyrimidin-4-yl]-amino}-ethanol;

dibutyl-[6-methyl-3-methylsulfanyl-1-(2,4,6-trichlorophenyl)-1H-pyrazolo [3,4-d]pyrimidin-4-yl}-amine;

butyl-ethyl-[6-methyl-3-methylsulfanyl-1-(2,4,6-trichlorophenyl)-1H-pyrazolo[3,4-d]pyrimidin-4-yl]-amine;

butyl-ethyl-[6-methyl-3-methylsulfanyl-1-(2,4,6-trichlorophenyl)-1H-pyrazolo [3,4-d]pyrimidin-4-yl]-amine;

butyl-cyclopropylmethyl-[6-methyl-3-methylsulfanyl-1-(2,4,6-trichlorophenyl)-1H-pyrazolo[3,4-d]pyrimidin-4-yl]-amine;

di-1-propyl-[6-methyl-3-methylsulfanyl-1-(2,4,6-trichlorophenyl)-1H-pyrazolo [3,4-d]pyrimidin-4-yl]-amine;

diallyl-[6-methyl-3-methylsulfanyl-1-(2,4,6-trichlorophenyl)-1H-pyrazolo[3,4-d]pyrimidin-4-yl]-amine;

butyl-ethyl-[6-chloro-3-methylsulfanyl-1-(2,4,6-trichlorophenyl)-1H-pyrazolo [3,4-d]pyrimidin-4-yl]-amine;

butyl-ethyl-[6-methoxy-3-methylsulfanyl-1-(2,4,6-trichlorophenyl)-1H-pyrazolo[3,4-d]pyrimidin-4-yl]-amine;

propyl-ethyl-[3,6-dimethyl-1-(2,4,6-trimethylphenyl)-1H-pyrazolo[3,4-d]pyrimidin-4-yl]-amine; or 4-(1-ethyl-propyl)-6-methyl-3-methylsulfanyl-1-(2,4,6-trimethylphenyl)-1H-pyrazolo[3,4-d]pyrimidine.

6. The method of claim 1, wherein said phobias are selected from the group consisting of agoraphobia, social phobia, and simple phobia.

7. The method of claim 1, wherein said stress induced pain perception is fibromyalgia.

* * * * *